US011123464B2

United States Patent
Yuds et al.

(10) Patent No.: US 11,123,464 B2
(45) Date of Patent: Sep. 21, 2021

(54) CALCULATING A DEPLETION TIME DURING DIALYSIS

(71) Applicant: Fresenius Medical Care Holdings, Inc., Waltham, MA (US)

(72) Inventors: David Yuds, Hudson, NH (US); Martin Joseph Crnkovich, Walnut Creek, CA (US); Ken Chhi, Fremont, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 373 days.

(21) Appl. No.: 16/012,945

(22) Filed: Jun. 20, 2018

(65) Prior Publication Data
US 2019/0388600 A1 Dec. 26, 2019

(51) Int. Cl.
*A61M 1/16* (2006.01)
*G01F 9/00* (2006.01)

(52) U.S. Cl.
CPC ........ *A61M 1/1607* (2014.02); *A61M 1/1613* (2014.02); *G01F 9/001* (2013.01); *A61M 2205/15* (2013.01); *A61M 2205/18* (2013.01); *A61M 2205/3317* (2013.01); *A61M 2205/3334* (2013.01); *A61M 2205/3386* (2013.01); *A61M 2205/502* (2013.01); *A61M 2205/583* (2013.01)

(58) Field of Classification Search
None
See application file for complete search history.

(56) References Cited

U.S. PATENT DOCUMENTS

| 2010/0069817 A1* | 3/2010 | Falkvall | A61M 1/1656 604/6.11 |
| 2013/0049974 A1* | 2/2013 | Crnkovich | A61M 1/1668 340/657 |
| 2014/0263064 A1* | 9/2014 | Jones | A61M 1/1609 210/647 |

FOREIGN PATENT DOCUMENTS

| EP | 2035059 | 3/2009 |
| WO | WO 2007/144427 | 12/2007 |

OTHER PUBLICATIONS

PCT International Preliminary Report on Patentability in International Appln. No. PCT/US2019/037424, dated Dec. 30, 2020, 7 pages.
International Search Report and Written Opinion in Application No. PCT/US2019/037424, dated Sep. 10, 2019, 9 pages.

* cited by examiner

*Primary Examiner* — Jonathan M Peo
(74) *Attorney, Agent, or Firm* — Fish & Richardson P.C.

(57) ABSTRACT

The disclosure relates to a dialysis machine that comprises a dialyzer, a fluid source, a first line connected to the fluid source, and a container containing bicarbonate. The container connects to the first line and the fluid flows from the fluid source, through the first line, to the container. The dialysis machine further includes a second line connected to the container, a flow rate sensor connected to at least one of the lines, a pressure sensor configured for detecting fluid pressure of the container, a display, and a data processing apparatus. The data processing apparatus is configured to receive signals from the flow rate sensor and the pressure sensor. The data processing apparatus is configured to calculate a size of the container based on the received signals.

17 Claims, 8 Drawing Sheets

| Dialysate flow QD (mL/min) | Bicarbonate Setting (mEq/L or mmol/L) | | | | | | | | | | | | | | | | |
|---|---|---|---|---|---|---|---|---|---|---|---|---|---|---|---|---|---|
| | 40 | 39 | 38 | 37 | 36 | 35 | 34 | 33 | 32 | 31 | 30 | 29 | 28 | 27 | 26 | 25 | 24 |
| 800 | 180 | 185 | 189 | 195 | 200 | 206 | 212 | 218 | 225 | 232 | 240 | 248 | 257 | 267 | 277 | 288 | 300 |
| 700 | 206 | 211 | 217 | 222 | 229 | 235 | 242 | 249 | 257 | 265 | 274 | 284 | 294 | 305 | 316 | 329 | 343 |
| 600 | 240 | 246 | 253 | 259 | 267 | 274 | 282 | 291 | 300 | 310 | 320 | 331 | 343 | 356 | 369 | 384 | 400 |
| 500 | 288 | 295 | 303 | 311 | 320 | 329 | 339 | 349 | 360 | 372 | 384 | 397 | 411 | 427 | 443 | 461 | 480 |
| 400 | 360 | 369 | 379 | 389 | 400 | 411 | 424 | 436 | 450 | 465 | 480 | 497 | 514 | 533 | 554 | 576 | 600 |
| 300 | 480 | 492 | 505 | 519 | 533 | 549 | 565 | 582 | 600 | 619 | 640 | 662 | 686 | 711 | 738 | 768 | 800 |
| 200 | 720 | 738 | 758 | 778 | 800 | 823 | 847 | 873 | 900 | 929 | 960 | 993 | 1029 | 1067 | 1108 | 1152 | 1200 |

900g

| Dialysate flow QD (mL/min) | Bicarbonate Setting (mEq/L or mmol/L) | | | | | | | | | | | | | | | | |
|---|---|---|---|---|---|---|---|---|---|---|---|---|---|---|---|---|---|
| | 40 | 39 | 38 | 37 | 36 | 35 | 34 | 33 | 32 | 31 | 30 | 29 | 28 | 27 | 26 | 25 | 24 |
| 800 | 240 | 246 | 253 | 259 | 267 | 274 | 282 | 291 | 300 | 310 | 320 | 331 | 343 | 356 | 369 | 384 | 400 |
| 700 | 274 | 281 | 289 | 297 | 305 | 313 | 323 | 332 | 343 | 354 | 366 | 378 | 392 | 406 | 422 | 439 | 457 |
| 600 | 320 | 328 | 337 | 346 | 356 | 366 | 376 | 366 | 400 | 413 | 427 | 441 | 457 | 474 | 492 | 512 | 533 |
| 500 | 384 | 394 | 404 | 415 | 427 | 439 | 452 | 465 | 480 | 495 | 512 | 530 | 549 | 569 | 591 | 614 | 640 |
| 400 | 480 | 492 | 505 | 519 | 533 | 549 | 565 | 582 | 600 | 619 | 640 | 662 | 686 | 711 | 738 | 768 | 800 |
| 300 | 640 | 656 | 674 | 692 | 711 | 731 | 753 | 776 | 800 | 826 | 853 | 883 | 914 | 948 | 985 | 1024 | 1067 |
| 200 | 960 | 985 | 1011 | 1038 | 1067 | 1097 | 1129 | 1164 | 1200 | 1239 | 1280 | 1324 | 1371 | 1422 | 1477 | 1536 | 1600 |

CALCULATING A DEPLETION TIME DURING DIALYSIS

TECHNICAL FIELD

This disclosure relates to a dialysis machine and a dialysis system that is capable of detecting a volume of an attached container. Additionally, the dialysis machine is capable of calculating a depletion time for treatment using the detected volume.

BACKGROUND

Dialysis is often prescribed for patients who are unable to clear his or her blood properly using his or her renal system (e.g., kidneys).

The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream across the membrane. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

In an HD treatment, a patient is connected to an extracorporeal blood circuit by inserting a venous bloodline and an arterial bloodline to draw intoxicated blood from the body and infuse the cleaned blood back into the body. A dialysis machine takes in the blood from the arterial line, and flows the blood past a semipermeable membrane or filter that is permeable to toxins and fluid. On the other side of the filter, dialysate flows in the opposite direction. The dialysate is a combination of acid, water, and other chemicals, the most notable of which is bicarbonate. The length of treatment time and concentrations of chemicals within the dialysate are prescribed by a physician and are inputted into the dialysis machine prior to beginning dialysis. The prescription includes a concentration of bicarbonate, flow rate, and treatment length, among other parameters and concentrations. Often the dialysate is mixed using fluids that are previously saturated with a specific substance. For example, bicarbonate solution is created by mixing fluid with powder bicarbonate concentrate. That bicarbonate solution can then be used to mix with other saturated solutions to create dialysate.

The saturated solution for a single substance can be readied by the machine by inserting a container into the dialysis machine and inputting all relevant information including the size of the container, the prescription, and additional patient data. The larger volume containers are able to support longer treatment sessions and/or increased flow rates. After initial connection to the machine, the dialysis machine fills the bags with water, dissolving the powdered bicarbonate, and creating a bicarbonate solution. The dialysis machine then moves the saturated bicarbonate solution to mix with acid solution and additional substances in a chamber, to create dialysate. After some of the solution is removed from the container, additional bicarbonate solution is generated to in turn, produce more dialysate. These containers are considered depleted when the bicarbonate or acid concentrate is depleted. Current machines test depletion of bicarbonate using conductivity sensors. To determine the proper volume of container, the patient or operator must consult a manual for a table that provides an approximate depletion time based on the prescribed flow rate and the prescribed bicarbonate concentration. An alarm or other form of user notification will occur when the bicarbonate level or the acid level is below 20%. When this occurs, the treatment must be paused and the operator must change one or both containers in order to proceed with treatment. It is preferred to ensure the bicarbonate or acid will last the entire treatment, to prevent stoppage of the treatment.

In use, an operator prepares the dialysis machine and the patient prior to enacting the treatment, which can be a time consuming process. It involves disinfecting the machine, the patient, and all apparatus interacting with the machine or the patient. A mistake in the setup may not be apparent until an alarm triggers during dialysis, if the dialysis machine is configured to test for these mistakes.

SUMMARY

In a first aspect, a dialysis machine comprises a dialyzer, a fluid source, a first line connected to the fluid source, a container containing bicarbonate, the container connected to the first line. The fluid flows from the fluid source, through the first line, to the container. The dialysis machine further comprises a second line connected to the container, a flow rate sensor connected to at least one of the lines, a pressure sensor configured for detecting fluid pressure of the container, a display, and a data processing apparatus configured to receive signals from the flow rate sensor and the pressure sensor. The data processing apparatus is configured for, based on the received signals, calculating a size of the container, based on the received signals and the calculated size of the container, calculating a concentration of a solution of bicarbonate and fluid flowing through the second line to the dialyzer, based on the calculated concentration, calculating an estimated time at which the bicarbonate will be depleted, and causing the display to present a visual representation of the estimated time at which the bicarbonate will be depleted.

In any embodiment, a fluid enters the container containing the solid bicarbonate and mixes with a portion of the solid bicarbonate to produce the solution of bicarbonate and fluid.

In any embodiment, the solution comprises dialysate.

In any embodiment, the pressure sensor is configured to send a signal to the data processing apparatus when a predetermined pressure of the container is measured by the pressure sensor.

In any embodiment, the predetermined pressure defines the container as full.

In any embodiment, the data processing apparatus measures is configured to measure a period of time, wherein the period of time is defined between an initiation of fluid flow into the container and the signal from the pressure sensor.

In any embodiment, the data processing apparatus uses the period of time, to determine the size of the container.

In any embodiment, the depletion time of the solution of bicarbonate is calculated using measurements from the flow rate sensor and from the calculated size of the container.

In any embodiment, a user comprising a user interface is configured to prompt a user to input a prescription, which includes a prescribed flow rate and a prescribed bicarbonate, into the dialysis machine.

In any embodiment, the data processing apparatus is configured to estimate the time at which the bicarbonate will be depleted using the flow rate sensor, the calculated size of the container, and the prescription inputted by a user.

In any embodiment, the data processing apparatus is configured to notify the user via the user interface if a treatment time, determined from the prescription, is longer than the calculated bicarbonate depletion time.

In any embodiment, the flow rate sensor, the pressure sensor, and a conductivity sensor are configured to provide feedback to the data processing apparatus.

In any embodiment, the visual representation of the estimated time at which the bicarbonate will be depleted, is updated using the feedback of the flow rate sensor, the pressure sensor, and the conductivity sensor.

In any embodiment, a leak from the container can be detected using the feedback from the flow rate sensor, the pressure sensor, and the conductivity sensor.

In any embodiment, the leak is detected by the pressure sensor measuring a decrease in pressure outside a threshold.

In any embodiment, the flow rate sensor comprises a volumetric pump.

In any embodiment, the fluid source comprises a volumetric chamber.

In another aspect a method comprises receiving a container of a definite volume, the container containing a concentrate, determining the volume of the container using a pressure sensor, a controller, a timer, and a fluid source upstream of the pressure sensor, calculating a depletion time in which the concentrate will be depleted from the container.

In any embodiment, the method comprises testing for the presence of a leak in the container and determine a flow rate of the leak, before calculating the depletion time.

In any embodiment, calculating the depletion time is based on the flow rate of the leak.

In any embodiment, the method comprises comparing the depletion time with a prescribed treatment time and notifying a user if the depletion time is less than the prescribed treatment time.

DETAILED DESCRIPTION

In some implementations, the dialysis machine is configured to determine the volume of a container of bicarbonate concentrate attached to the dialysis machine for the production of dialysate. The container may be disposable with a prefix volume of bicarbonate powder within the container. The container may be opaque or solid such that a clear view of the powder may not be provided. Additionally, the container is located within the dialysis machine during use so the operator or user may not view the amount of bicarbonate in the container when the dialysis machine is operating.

The dialysis machine includes a timer, a pressure sensor, a container, and a fluid source (e.g., a volumetric chamber) to determine the volume of a container. The volumetric chamber, located within the hydraulic system, monitors the amount of fluid pumped through each cycle. In some implementations, the dialysis machine may use a volumetric pump, in place of the volumetric chamber, to determine the volume of the container. The volumetric pump, also known as a concentrate pump, pumps a mixture of a concentrate and water into a chamber for mixing dialysate. Alternatively, the volume may be determined using a flow sensor and pressure sensor. Volume determination may use a pressure threshold, a time range, a flow rate threshold, or a combination thereof. Additional methods, such as weight or optical methods, for volume determination are also intended to fall within the scope of the disclosure.

In addition to determining the volume of an attached container, the dialysis machine may also determine the presence of a leak, particularly if the leak effects the method of volume determination, for example if the leak was large enough to create a pressure drop when a constant pressure is prompted, or if the container takes longer than a predetermined range of time to fill. Leak detection may be routinely checked during dialysis.

To perform a dialysis treatment, the container is first inserted into the dialysis machine by connecting an inlet of the container to a fluid source via a first tube. The container is also connected an outlet to a mixing chamber via a second tube. The container is filled with fluid from the fluid source until a specific pressure is reached. In some implementations, the pressure is 150 mmHg. In some implementations, the water is warm to promote dissolution of powdered bicarbonate and fluid saturation. The water is then removed from the container using the tube connected to the outlet and the pressure drops. Fluid removal terminates when the pressure is around 50 mmHg. At the inlet, fluid begins to refill the container. The pressure increases as no fluid is being removed while the container fills. Once the threshold of 90 mmHg is reached, the saturated fluid is removed and the pressure decreases to 50 mmHg. The system cycles through the upper and lower pressure thresholds, adding warmed fluid to increase the pressure to 90 mmHg and removing water to decrease the pressure to 50 mmHg. Some implementations may use different pressure thresholds that are not referenced in this disclosure but are intended to fall within the scope of the disclosure.

A leak may be detected using a pressure sensor by measuring the pressure of the container at time when pressure is prompted to be constant. A leak may be present if the pressure sensed by the sensor is decreasing, rather than remaining constant as prompted. Alternatively, a pressure sensor and flow sensor may indicate a container leak. The flow sensor measures the flow rate when fluid as removed, decreasing the pressure in the container from the upper threshold to the lower threshold. A timer measures the amount of time for container to decrease the pressure from the upper threshold to the lower pressure threshold. As the flowrate and amount of time is known, a volume of fluid flowing from the container can be calculated by multiplying the two values. The volume calculated can be compared to a known volume range of fluid flowing through the outlet during leakless operation. If the volume calculated is not within this range, a leak may be present.

The dialysis machine is also configured to detect the time at which bicarbonate concentrate will be depleted using the volume determination and the prescription inputted into the dialysis machine. The prescription includes a flow rate, treatment time, and a bicarbonate level. The dialysis machine is configured to compare the calculated depletion time with the prescribed treatment time. As pausing the dialysis is undesired, the depletion time should be a greater time length than the prescribed treatment time, to avoid replacing the bicarbonate container midtreatment. The dialysis machine compares the length of depletion time and the length of treatment time. The treatment continues as normal when the depletion time is greater than the treatment time. The dialysis machine will notify or alert the user when the depletion time is less than the treatment time. In some implementations, the dialysis machine may advise the user to increase the size of the container. More so, the dialysis machine may advise the user to insert a container larger than a calculated volume. The calculated volume suggested by the dialysis machine is the volume at which the treatment time is equal to the depletion time. This volume may not correspond with an available container volume. For example, the volume suggested could be 872 g. In some implementations, the notification may require a user confirmation to continue with the dialysis.

The depletion time and treatment time are displayed on a user interface located on the dialysis machine. In some implementations, the time elapsed in the treatment time and the time remaining in treatment time may also be displayed on the user interface. The time elapsed in the treatment time and the time remaining in the depletion time are additionally displayed. In some implementations a graphical or visual measure of depletion time left and treatment time elapsed, is displayed on the user interface.

In some implementations, the depletion time is recalculated at intervals. The depletion time may be recalculated using a conductivity sensor, or additional sensors.

A dialysis machine can be configured to detect a volume of an attached container. The type of container used for some types of dialysis (e.g., peritoneal dialysis [PD] or hemodialysis [HD]), contains an amount of concentrate that can be diluted and added to other diluted or undiluted substances to produce a dialysate. The container commonly contains bicarbonate concentrate, but other substances might be used. For example, the container may instead contain acid concentrate or any other concentrate used to produce the dialysate. In some implementations, the dialysis machine is configured to determine the volume of a container from a list of available volumes compatible with the dialysis machine. For example, the containers may be available in five different volumes and the dialysis machine is programmed with properties of each of the available volumes, such as fill time. The dialysis machine contains multiple sensors that can be used to determine features of the container, such as the volume or the presence of a leak. The processor of the dialysis machine can determine these features using a pressure sensor, a flow sensor, or a combination of a flow sensor and a pressure sensor. The processor is able to determine the volume of the container and sense the presences of a leak using data from the sensors in combination with a provided prescribed flow rate and concentration.

Figure 1:
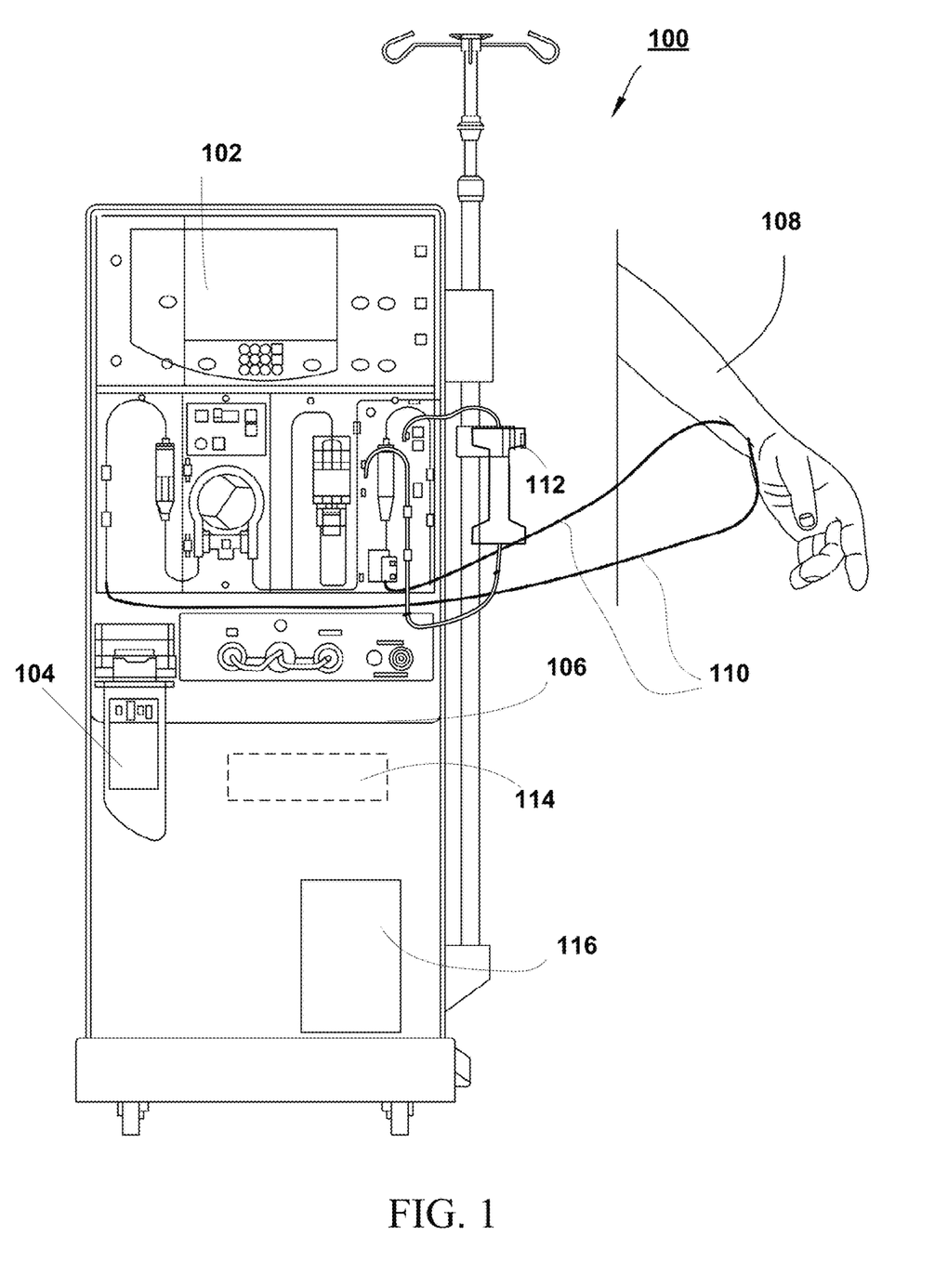
FIG. 1 shows a dialysis system during a dialysis session of a patient.

FIG. 1 illustrates a dialysis system 100 in which a patient 108 is connected to a dialysis machine 106 using a venous bloodline 100 and an arterial bloodline 100. The system 100 shown here is an HD system, but other kinds of systems could be used. The system 100 comprises a dialysis machine 106, a dialyzer 112, a container 104, a user interface 102, a processor 114, and a fluid source 116. The dialyzer 112, dialysis machine 106, arterial and venous bloodlines 110 are in fluid communication with each other, so that an extracorporeal blood circuit is created. The extracorporeal blood circuit is supported and controlled by the processor 114, user interface 102, and further comprises a fluid source 116, and a container 104.

Blood from the patient flows from the venous bloodline into the extracorporeal blood circuit, where the blood is cleared of toxins, and flows back into the body via the arterial bloodline. While in the extracorporeal blood circuit, the blood flows through the dialyzer 112, which is configured to remove toxins and excess fluid in the blood. The dialyzer 112 is split into two chambers in which the blood of the patient flows in one direction and a dialysate produced by the dialysis machine flows in another. The two chambers are separated by a semipermeable membrane. Toxins and excess fluid move from the blood to the dialysate chamber, often due to a concentration gradient. The dialysate is produced by mixing the contents of the containers with additional fluid and substances. The concentrations and flow rates of the dialysis are prescribed by a medical professional. Different concentrations and flow rates can vary the length of treatment and impact on the patient. For example, a high flow rate may result in a shorter treatment time but may be more difficult for the patient.

The container is connectable and disconnectable from the dialysis machine. The container is connected to the machine via connecting lines and tubes. Some of the tubes connected to the container are responsible for adding or removing fluid into and from the container. The dialysis machine is configured to connect lines and tubes of the dialysis machine to a connector on the container. The connector is similar for every volume of container provided, allowing for similar connection attachment procedures regardless of the container volume. Multiple container volumes are available to the operator. For example, the dialysis machine may connect to containers with volumes of 650 mg and 900 mg.

Figure 2:
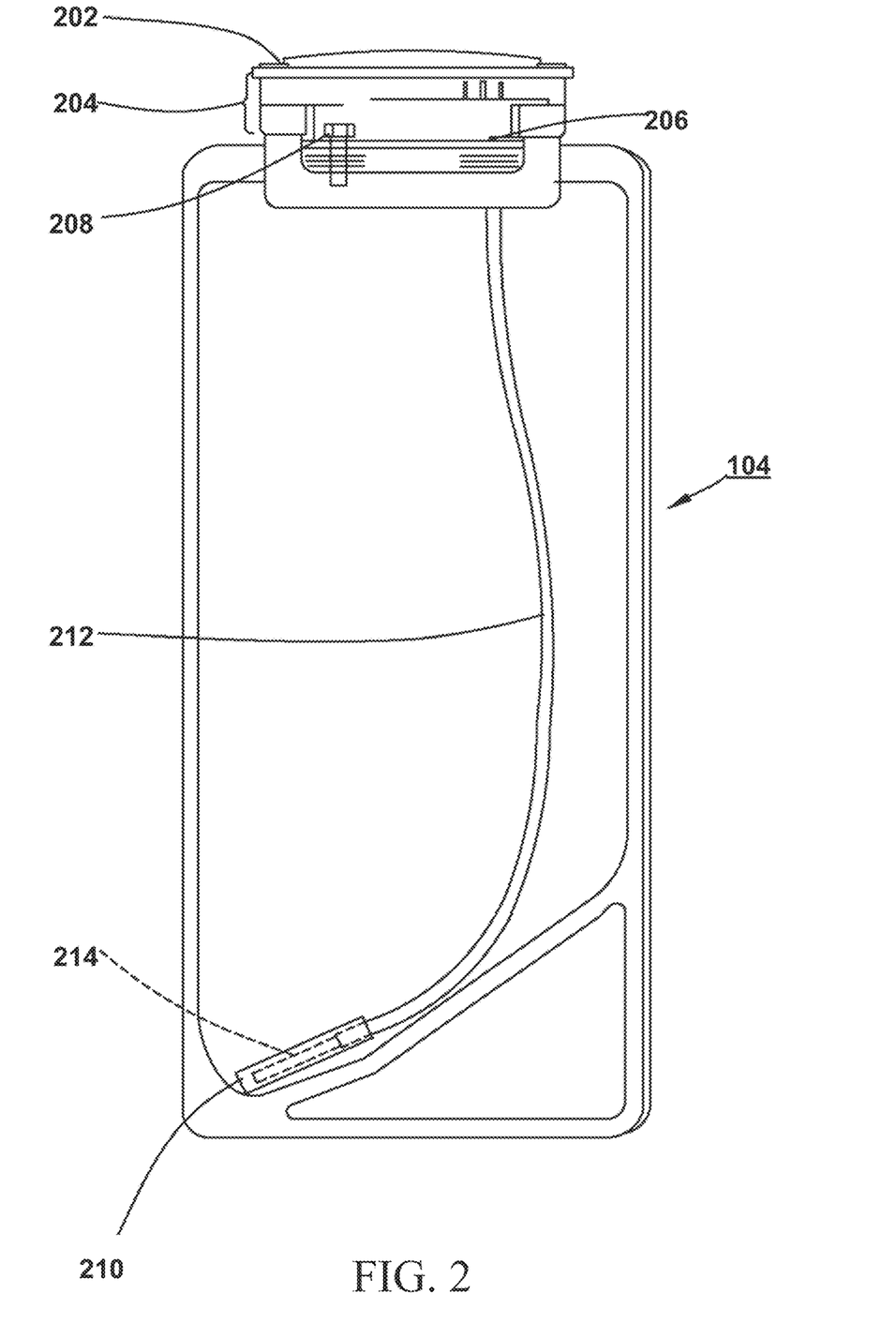
FIG. 2 shows a container connected to a dialysis machine within a dialysis system.

FIG. 2 illustrates a container 104 configured to be inserted into the dialysis machine 106 and containing a substance. For example, the substance can be a powder concentrate that is dissolvable with a fluid to create a saturated solution. The dialysis machine 106 is configured to create a saturated solution by flowing fluid into the container 104, via an inlet 208 that is integrated into the connector 204 of the container 104. The inlet 204 also connects to a fluid source. The dialysis machine is also configured to remove the saturated fluid from the container 104 via an outlet 206 integrated into the connector 204, and transport it to a location for mixing with other substances. After being removed from the container, the saturated solution mixes with additional solutions to create a dialysate or other dialysis fluid. The dialysate then flows through the dialyzer to clear the blood of toxins, and is expelled into a waste receptacle.

To prepare the dialysis machine, the operator inserts the container 104 into the dialysis machine 106, connecting the connector 204 of the cap 202 to the fluid line of the dialysis machine 106. The connector 204 facilitates the connection of the inlet 208 port to the fluid source 116 and facilitates the connection of the outlet 206 port to the dialyzer 112. The fluid source 116 provides temperature appropriate fluid for mixing. A warm fluid may allow for improved dissolution and a more saturated solution. The fluid flows into the container 104 from the inlet 208. The inlet 208 is in communication a pressure sensor (not shown) that is configured to measure the pressure within the container 104. Once the pressure sensor measures a predetermined pressure, the container 104 is identified as full by the processor. The processor sends a signal to a fluid source pump (not shown) disposed upstream of the inlet 208 and/or a fluid valve (not shown) disposed upstream of the inlet 208, to stop fluid flow into the container 104. The fluid valve may prevent fluid flow by impeding the fluid line upstream of the inlet 208 such that fluid may not pass into the container 104. The fluid stops entering at the inlet 208. After fluid in-flow stops, the fluid is drawn from the container 104 through an opening 210 of a tube 212 connected to the outlet 206. The opening 210 is covered by a filter 214 to ensure only fluid is removed from the container 104. The saturated fluid continues along the fluid line to combine with other substances to produce dialysate. In some implementations, the substance within the container 104 is bicarbonate. In some implementations, the substance is an acid compound used in dialysis. In some implementations, the substance within the container 104 is a liquid concentrate.

Figure 3:
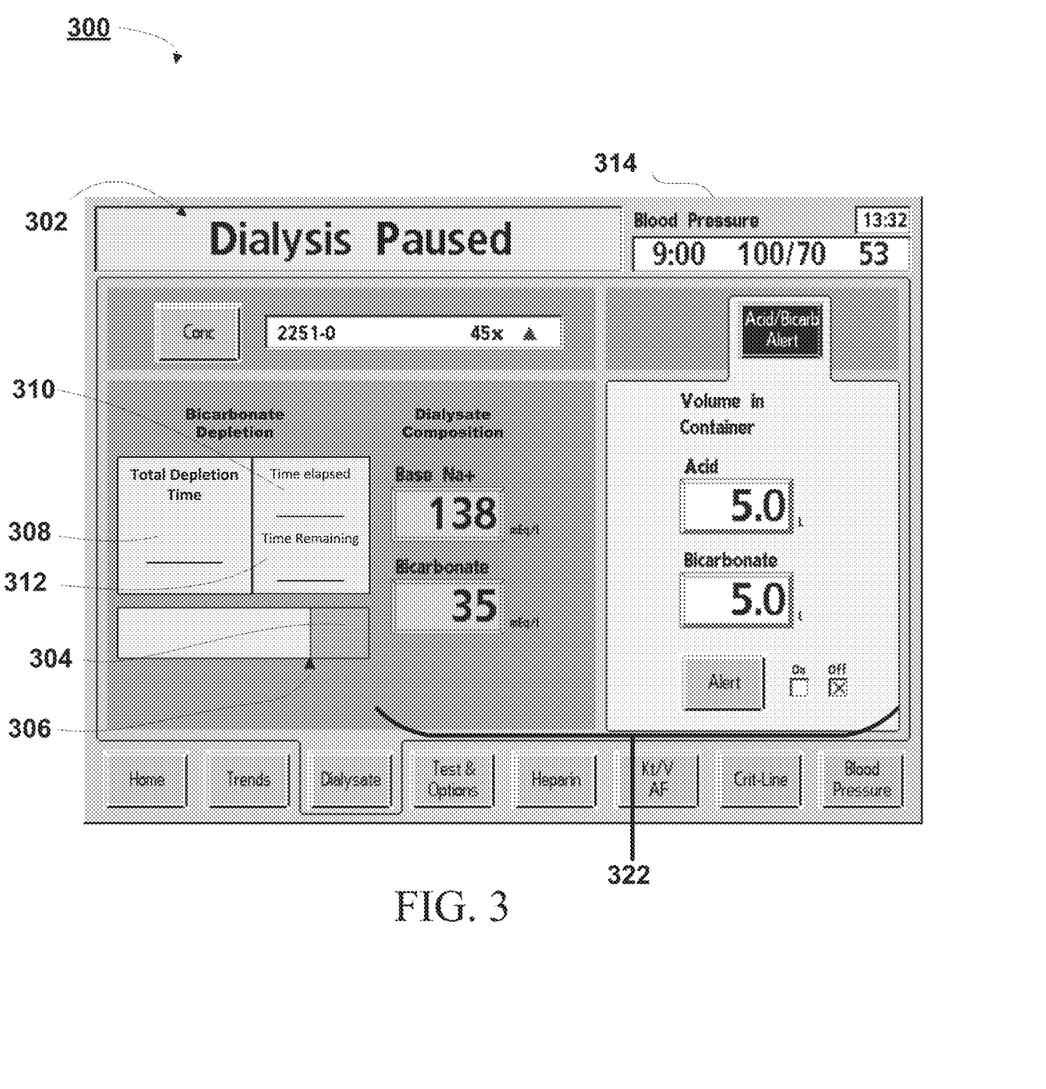
FIG. 3 shows a user interface displaying the dialysate concentrations and the calculated depletion times.

FIG. 3 illustrates a user interface 300 of the dialysis machine 106. The user interface 300 may be an example of the user interface 102 shown in FIG. 1. The user interface 300 is configured to display information 302 related to the dialysis. It is the primary interface for user interaction and notifications. At the user interface in FIG. 3, the prescription 322 is entered and displayed. The display also shows blood pressure 314, in addition to other treatment and patient information. The user interface 300 displays the depletion time left 308 in a dialysis treatment and/or the treatment time calculated 312 for a determined container volume. The time elapsed 310 in the treatment and the time remaining in the treatment 312 are displayed next to the total depletion time. Additionally, a visual image of depletion or treatment time is displayed. An arrow 306 notes the amount of time elapsed and the bar 304 defines the total treatment time. The user interface 300 may display only the graphical treatment time model or may alternatively only display the text-based model. The models may be updated as the dialysis treatment continues to ensure accurate information.

Figure 4:
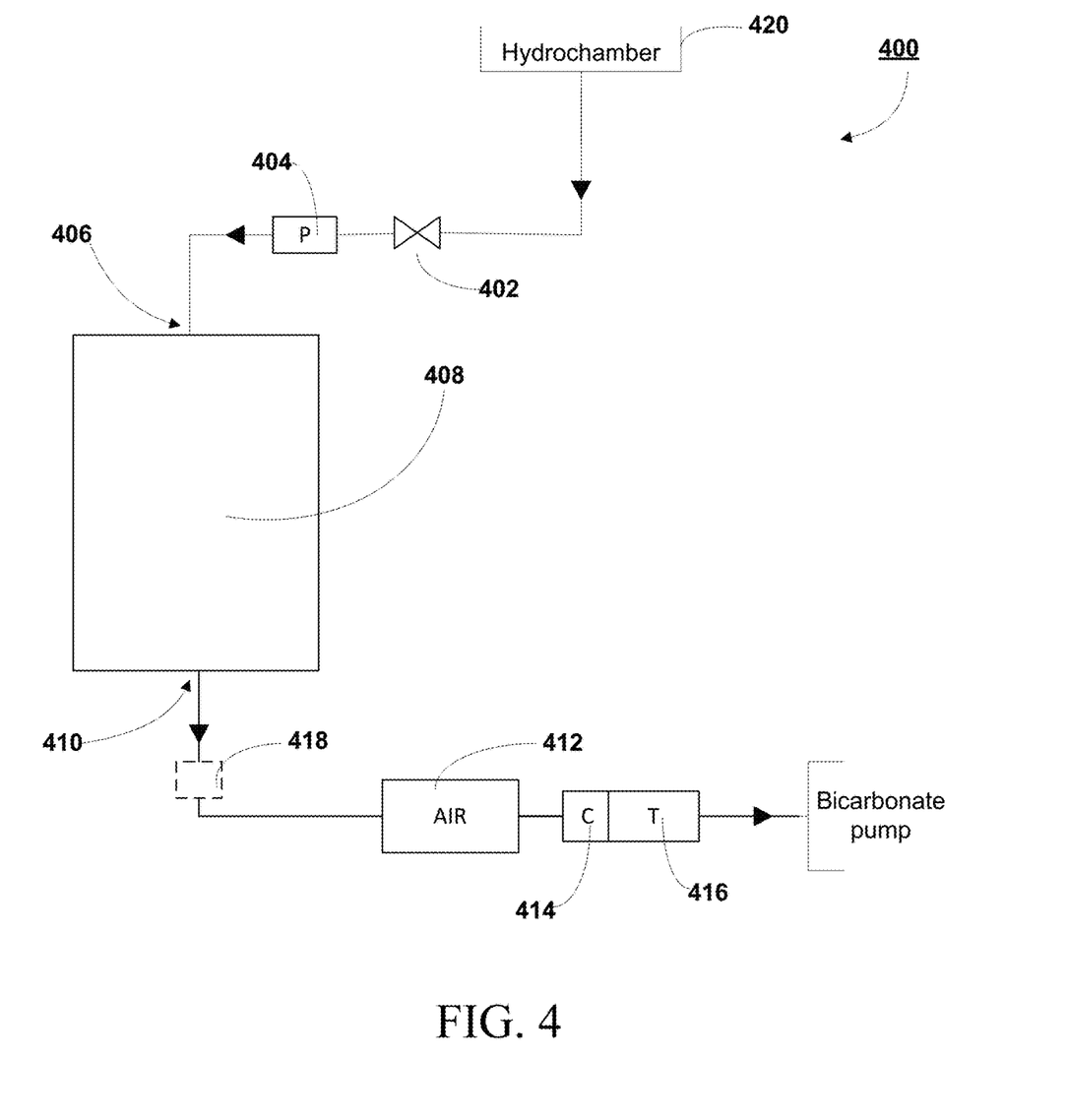
FIG. 4 shows a simplified dialysis machine flow line.

FIG. 4 illustrates a dialysis flow line 400 including the fluid source 116, a valve 402, the pressure sensor 404, the container 104, a flow rate sensor 418, an air sensor 412, the conductivity sensor 414, a temperature sensor 416, and a bicarbonate pump 422 leading to a dialyzer 112. The container 104 includes the inlet port 406 and the outlet port 410 that completes the fluid line 400 so that fluid may flow from the fluid source 116 into the bicarbonate pump. FIG. 2 also illustrates the inlet port 406 and outlet port 410, in a more detailed illustration of the container 408. A hydrochamber 420 leads to the valve 402. The hydrochamber 420 may be an example of the fluid source 116 shown in FIG. 1. The valve 402 may open or close depending on the signal from the processor 114. The position of the valve 402 is controlled by a processor 114 and is initially open. The pressure sensor 404 is also connected to the processor 114 and is configured to send signals to the processor 114 regarding the pressure within the container 408. The container 408, as described in FIG. 2, contains bicarbonate powder and is in fluid communication with the hydrochamber 420 and the valve 402. A flow sensor 418 is shown connected to the outlet port 410 of the container 408 and to the processor 114. The flow sensor 418 is configured to send signals containing flow rate information at the outlet port 410 of the container 408 to the processor. An air sensor 412 is located on the flow line 400 downstream from the outlet port 410 and is configured to detect air in the fluid. The air sensor 412 is connected the processor 114 and configured to send air detection information to the processor. If air is detected in the system, the dialysis machine 106 will notify the operator and may pause treatment. The conductivity sensor 414 is configured to sense the conductivity of a fluid in the line downstream of the outlet 410 and is connected to the processor. The conductivity sensor is sends signals containing conductivity information to the processor. The conductivity information can be used to determine when Bicarbonate levels are below a threshold, for example 20% depleted. The temperature sensor 416 measures the temperature of the saturated fluid and it located downstream of the outlet port 410 and upstream of the bicarbonate pump. The temperature sensor 416 is connected to the processor 114 and is configured to transmit temperature information to the processor.

The dialysis machine 106 uses at least one sensor to determine if the container 408 is leaking. The dialysis machine may detect a leak using the pressure sensor 404 and/or the flow rate sensor 418. A leak may be discovered using only a pressure sensor 404 by measuring the pressure when fluid is prevented from exiting or entering the container 104. The pressure at this time should be constant. Therefore, if the pressure is decreasing over time, there is a leak present. More so, the flowrate of the leak can be determined by noting the rate in pressure decrease. This can allow more accurate depletion time calculation because the flow rate out of the container due to both the leak and the removal through the outlet 206 are known. An operator will be notified of the leak (e.g., on the user interface 300 or by use of an alarm) so that the operator may replace the leaking container 408.

A leak may also be determined using a pressure sensor 404 and a flow rate sensor 418. This leak determination using both sensors does not require a constant pressure. Furthermore, the method using the pressure sensor 404 and flow rate sensor 418 can be used while fluid is removed from the container 104. The flow rate sensor 418 is located downstream of the container 408 and the pressure sensor 404 is located upstream from the inlet port 406. The pressure sensor 404 measures a change in pressure as the saturated fluid is being removed from the container 408. As in the previous leak determination, the decrease in pressure can be used bicarbonate to determine a flow rate out of the container 408. This exit flow rate measured by the pressure sensor encompasses both the flowrate exiting the outlet 206 and the flow rate exiting the leak, if present. The flow rate sensor 418 downstream of the outlet port 410 measures only the flow rate exiting the outlet 206. If the pressure calculated flow rate and the actual downstream flow rate are equal, there is no leak present. If the pressure calculated flow rate is greater than the downstream flow rate, the container 408 has a leak. The flowrate of the leak can be calculated by subtracting the slower, downstream flowrate from the total, pressure calculated exit flow rate. This allows the depletion time to recalculate, factoring in the leak, and will give the operator advanced notice of the accelerated depletion time.

A leak may also be determined using a flow rate sensor 418 downstream of the outlet 206 port. The flow rate sensor 418 will send measurements of the flowrate downstream of the outlet 410 to the processor 114. The flow rate entering at the inlet will be the same regardless of the leak, however the container 408 cycles through pressure changes; wherein water flows into the container 408 until the container 104 reaches a specified pressure and the water is removed from the container 408 until a specified pressure. The flow rate downstream therefore experiences moments of no fluid flow and moments of peak fluid flow. A total volume may be calculated by integrating a flow rate curve that can be generated by taking interval measurements of the flow rate. A total volume flowing though the flow sensor is compared to a known reference volume range. If the container has a leak, the integral of the flow rate curve will be smaller than the reference volume range, as less fluid would be flowing through the sensor as a result of the leak. Note that the integral of the actual flow sensor curve may have similar values (volumes) for each cycle of refill and removal. If the volume is less than the known range for the determined volume, the container has a leak.

Figure 5:
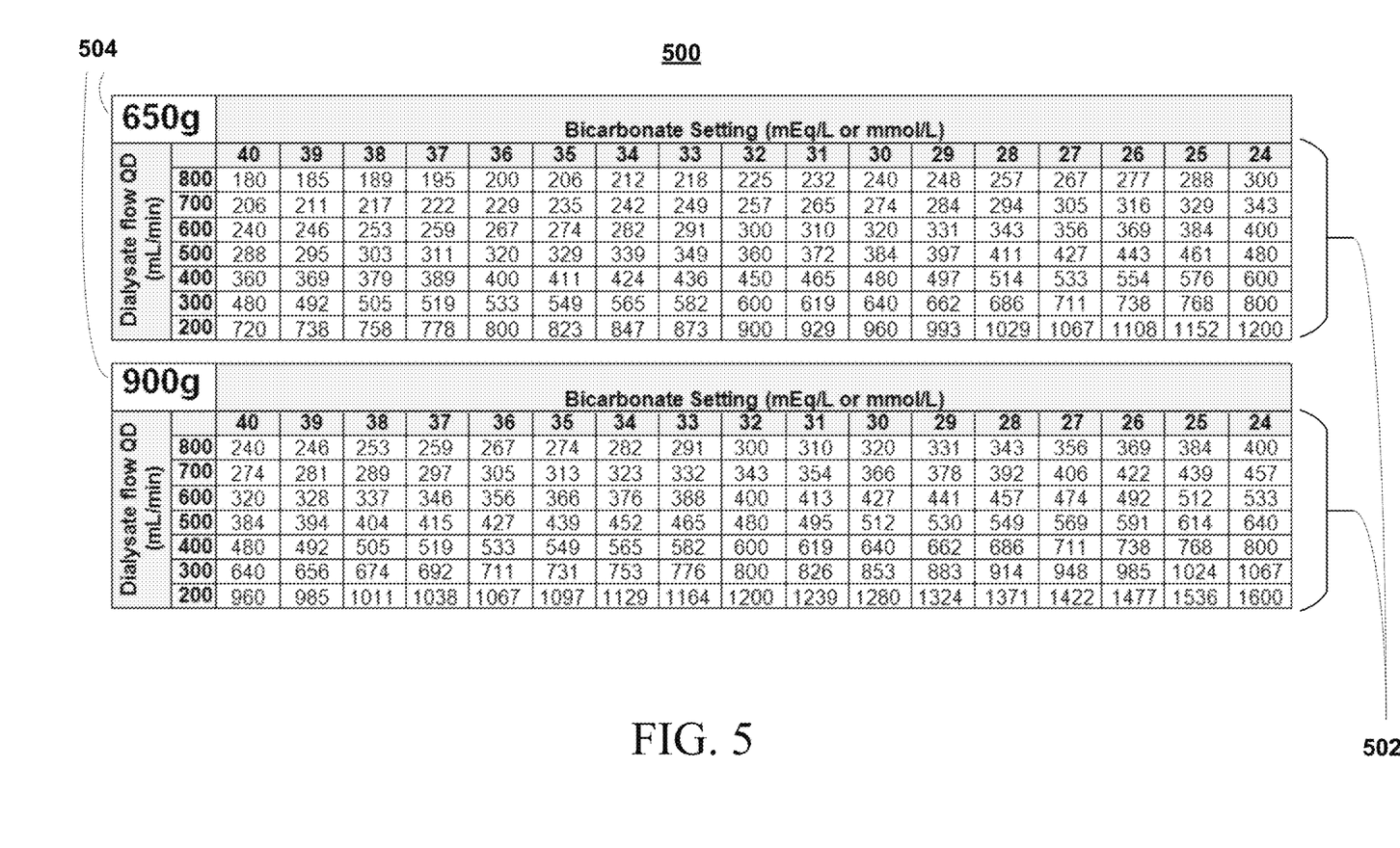
FIG. 5 shows a table of bicarbonate depletion times for a give prescribed flow rate and prescribed bicarbonate setting.

FIG. 5 illustrates a bicarbonate table 500 in the operating manual of a dialysis machine 106. The table 500 is used to manually finding the depletion time by first knowing the volume of the container 504, and using the level of bicarbonate and the flow rate, find the approximate depletion time 502. The table 500 is capable of demonstrating approximate depletion times 502 with known volumes 504. The treatments are highlighted if the depletion time is over 10 hours.

Figure 6:
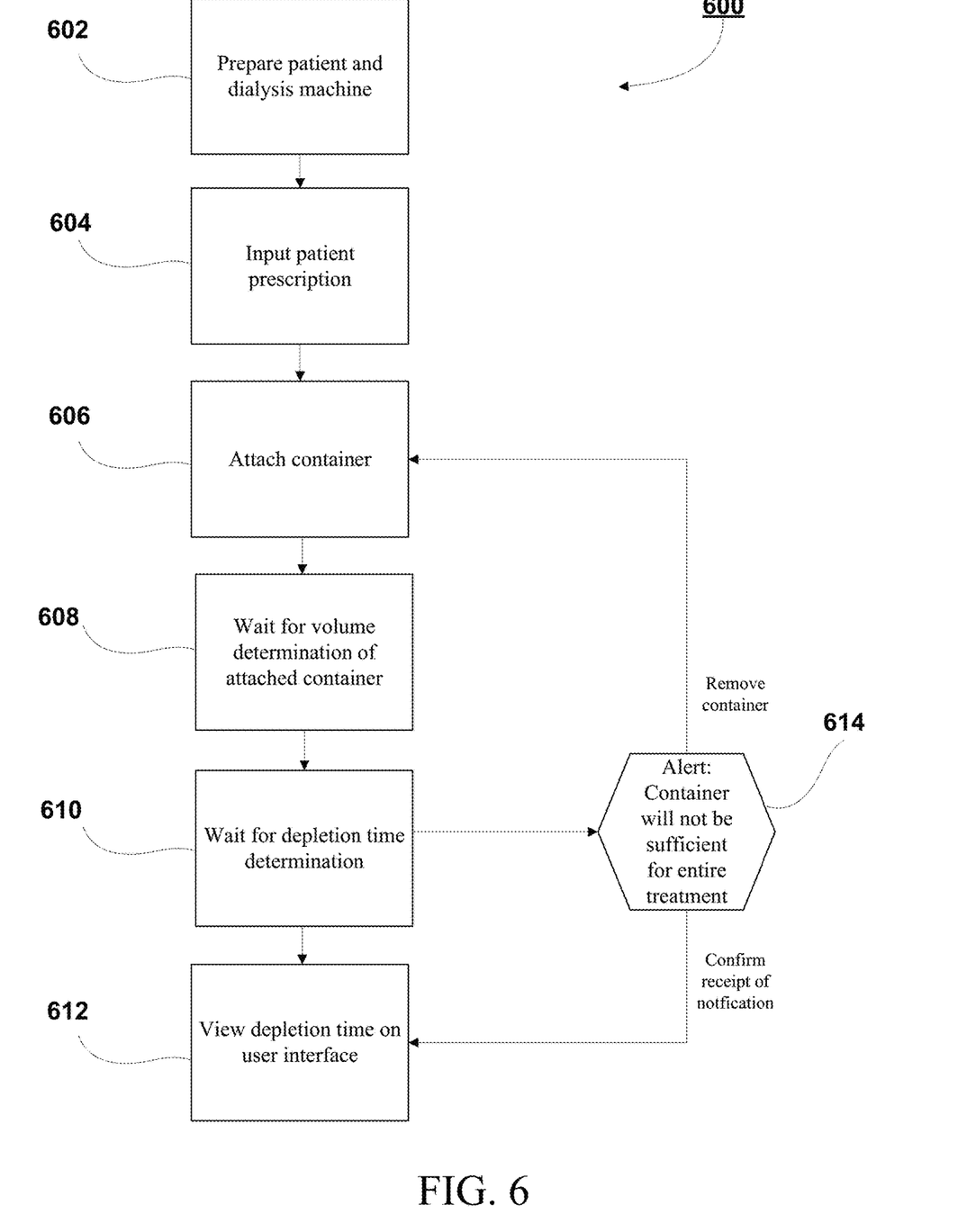
FIG. 6 shows a procedure for an operator of the dialysis machine.
Figure 7:
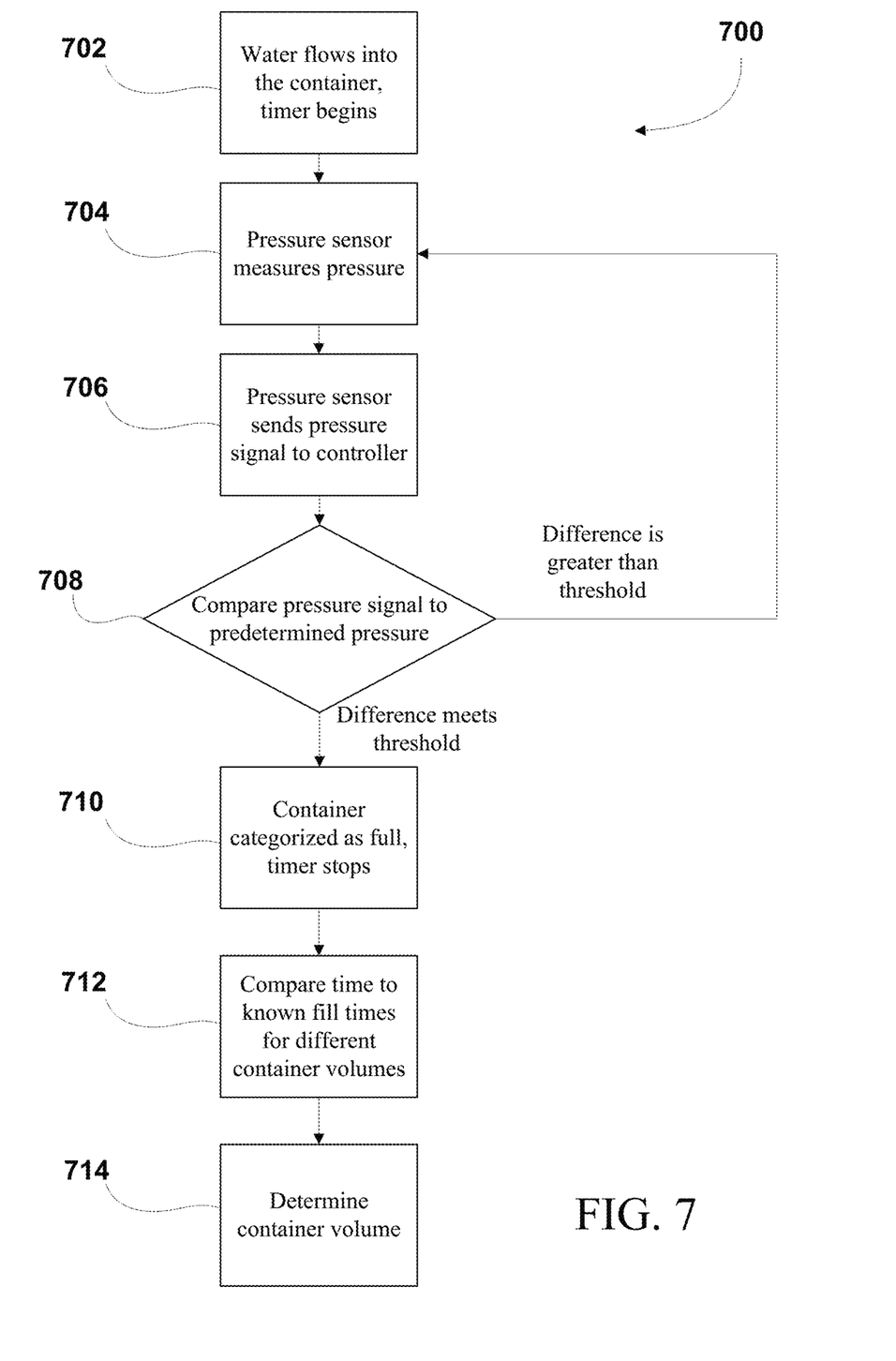
FIG. 7 shows a procedure for the dialysis machine to determine the volume of the container.
Figure 8:
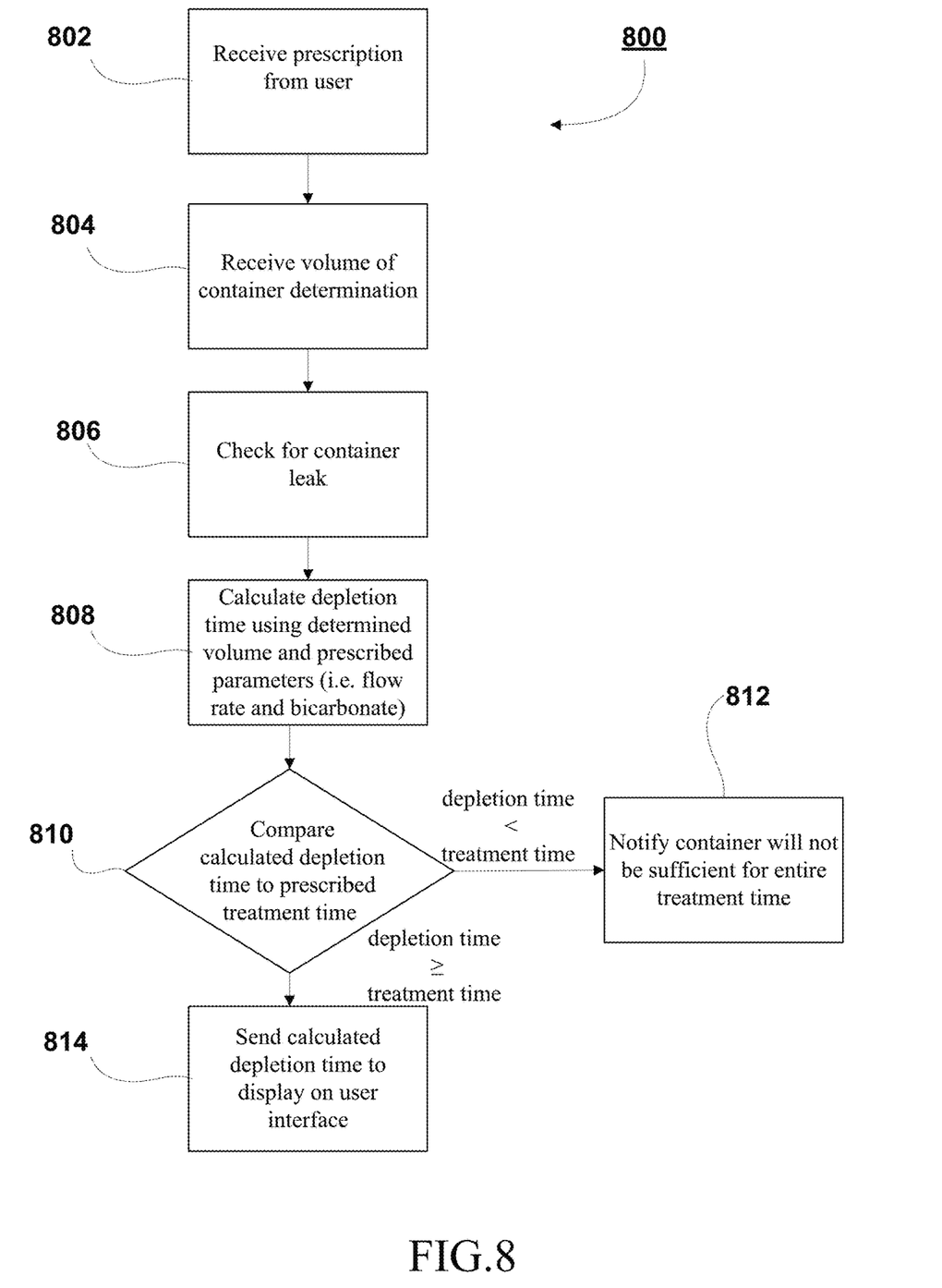
FIG. 8 shows a procedure for the dialysis machine to calculate the depletion time and display the depletion time.

FIGS. 6-8 show flowcharts representing procedures 600, 700, 800, related to the operation of the dialysis system 100. FIG. 6 illustrates a high-level operator procedure 600, while FIG. 7 and FIG. 8 illustrate procedures 700, 800 of a dialysis machine.

In FIG. 6, an operator prepares the dialysis system 602 and inputs the prescription of the patient 604, including a flow rate, a bicarbonate level, and a treatment time. The user then selects a container containing bicarbonate and inserts the container 606 in into the dialysis machine. The container is connected to the dialysis machine using the connector 204 shown in FIG. 2. The dialysis machine determines the volume 608 of the container and the depletion time based on the determined volume 610 and the prescribed parameters. Ideally, the depletion time is greater than the treatment time, meaning a change of container will not be necessary mid treatment. The treatment will continue as normal 612. If the depletion time is less than the treatment time, the user will be notified 614 (e.g., using the user interface 102 depicted in FIG. 3). The notification 614 may note the length of depletion time calculated for the volume.

If the depletion length is shorter than the treatment length, there is not enough bicarbonate to last the entire treatment. To avoid pausing the dialysis machine 106 in the middle of a dialysis treatment, the operator will have the option to retrieve a larger volume container 104 and insert it into the dialysis machine. Inserting a new container returns the dialysis machine to the volume determination step 608 and depletion calculation step 610.

In some treatments, the bicarbonate is not necessary for the entirety of the treatment. For example in sequential ultrafiltration dialysis, the treatment does not require dialysate for the entirety of the treatment but does require dialysate for a portion of the treatment. The operator may use professional knowledge to override the notification and continue with dialysis treatment. In this case, it is particularly useful for the dialysis machine to display the calculated depletion time in the notification or alert. Alternatively, a larger volume of container may not be immediately available in the dialysis clinic. In this case, the operator may override the notification. The depletion time is still useful information to display in the notification, as it can inform the operator when the container must be changed and/or may notify the operator of a leak within the container.

FIG. 7 presents a more detailed procedure of the volume determination step 606 (in FIG. 6). The volume may be determined using a pressure sensor. The dialysis machine prompts the hydrochamber and an upstream pump to flow fluid through the fluid line in the direction of the arrows in FIG. 4. The processor also prompts for a fluid valve upstream of the container to be opened. A timer is started 702. The fluid flows into the container and the pressure beings to rise. The pressure sensor measures 704 the rise of the container pressure and notifies the processor at interval time periods 706. The processor compares 708 the measured pressure to a reference pressure. When the reference pressure is measured by the pressure sensor, the timer stops and fluid flow stops by closing the valve 710. The time measured by the timer is analyzed and compared 712 to known time ranges for known volumes. For example if the 900 g volume of container may have a fill time range between X and Y. If time measured, t, falls between X and Y, the dialysis machine determines 714 that the volume of the attached container is 900 g.

If t falls below X and Y, the volume is not 900 g. If t lies above the range from X to Y, the volume may be larger or the container may contain a leak. A leak may be detected by holding the container at a constant pressure, preventing fluid addition or removal of fluid via the inlet or the outlet. If the pressure decreases, the container has a leak. If the pressure remains constant, the container does not have a leak. In the determination that the container has a leak, a notification will inform the operator via the user interface. In the case that t does not fall into a known reference range of any other volume and the container is not leaking, the user will be informed via the user interface that volume determination has failed.

As previously discussed, the dialysis machine may use alternative or additional methods to determine if a leak is present. Leak detection may occur using a pressure sensor, a flow rate sensor, or a pressure sensor and a flowrate sensor. Leak determination may also use one or more of these methods at one time, or may use different methods of leak detection at different steps in the procedure. For example, the dialysis machine may initially use leak determination with a pressure sensor for the initial set up but may use leak detection with a flow sensor when the dialysis machine begins cycling.

The upper and lower pressure thresholds for the initial pressure may be less than 150 mmHg. The upper pressure threshold when the dialysis machine adds fluid to the container may be greater than 90 mmHg. The lower pressure threshold when the dialysis machine removes fluid from the container, may be less than 50 mmHg.

FIG. 8 depicts a procedure for the calculation of depletion time 800. The operator inputs the container 104 and the prescription 802 of the patient into the dialysis machine manually or using a user identification mechanism. For example an id card or user identification number. The dialysis machine determines the volume 804 and checks for a leak within the container 806. If the container does not have a leak, the dialysis machine 106 calculates 808 the depletion time using the following equation:

$$t(s, Q_d) = k_0 M_{bc} \frac{1000}{s Q_d}.$$

The variable t is the depletion time in minutes; s is the bicarbonate setting in mEq/g; $Q_d$ is the dialysate flow rate in mL/min; Mb is the bicarbonate mass in g. In some embodiments, the mass is 650 g or 900 g depending on the container volume inserted into the dialysate machine. Note that the total flow rate is equal to the sum of $Q_d$ and $Q_i$ where $Q_i$, where is the flow rate of an infusate pump. In some embodiments, the total flow cannot exceed 1000 mL/min. The depletion time is then compared 810 to the treatment time inputted with the prescription 802. If the depletion time is greater than the treatment time, the depletion time will display 814 on a user interface (e.g., the user interface 102 shown in FIG. 4). If the depletion time is less than the treatment time, the operator will be notified 812 and prompted to change the container, adjust the prescription, or continue with treatment.

Changing the container will result in the volume determination 608 and the depletion calculation 610 to be reexecuted. Adjusting the prescription will prompt the depletion time calculation 610 to be reexecuted.

Additionally, the user interface may provide a notification displaying alternative prescriptions that lower the prescribed flow rate, lower the bicarbonate level, or shorten the treatment time. These options provide equal or greater depletion time to treatment time, allowing the treatment to proceed without a pause in the treatment to change a depleted container. The user interface 102 may also display the calculated depletion time if no variables are adjusted. Confirming the notification ensures the operator is aware of potential complications with the dialysis and allows the operator ample time to account for potential treatment interventions. For example preparing a second bag to switch mid treatment when the depletion time is expired. This may be useful particularly when large container volumes are out of stock or when the treatment center is busy.

The treatment setup or initiation may continue when the depletion time is calculated to be larger than or equal to the treatment time or the operator overrides the notification by confirming receipt. The depletion time and both elapsed treatment time and remaining treatment time, will display on the user interface. The graphical treatment time remaining also displays on the interface.

Implementations of the subject matter and the functional operations described above can be implemented in various types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of nonvolatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments of the invention have been described. Nevertheless, it will be understood that various modifications may be made without departing from the spirit and scope of the invention. Accordingly, other embodiments are within the scope of the following claims.

What is claimed:
1. A dialysis machine comprising:
a dialyzer;
a fluid source;
a first line connected to the fluid source;
a container containing bicarbonate, the container connected to the first line, wherein a fluid flows from the fluid source, through the first line, to the container;
a second line connected to the container;
a flow rate sensor connected to at least one of the first line and the second line;
a pressure sensor configured for detecting fluid pressure of the container;
a display; and
a data processing apparatus configured to receive signals from the flow rate sensor and the pressure sensor, the data processing apparatus configured for:
based on the received signals, calculating a size of the container;
based on the received signals and the size of the container, calculating a concentration of a solution of bicarbonate and fluid flowing through the second line to the dialyzer;
based on the concentration, calculating an estimated time at which the bicarbonate will be depleted; and
causing the display to present a visual representation of the estimated time at which the bicarbonate will be depleted.

2. The dialysis machine of claim 1, wherein the fluid enters the container containing the bicarbonate and mixes with a portion of the bicarbonate to produce the solution of bicarbonate and fluid.

3. The dialysis machine of claim 1, wherein the solution comprises dialysate.

4. The dialysis machine of claim 1, wherein the pressure sensor is configured to send a signal to the data processing apparatus when a predetermined pressure of the container is measured by the pressure sensor.

5. The dialysis machine of claim 4, wherein the predetermined pressure corresponds to the container being full.

6. The dialysis machine of claim 4, wherein the data processing apparatus is configured to measure a period of time, wherein the period of time is defined between an initiation of fluid flow into the container and the signal from the pressure sensor.

7. The dialysis machine of claim 6, wherein the data processing apparatus uses the period of time to determine the size of the container.

8. The dialysis machine of claim 1, wherein the estimated time at which the bicarbonate will be depleted is calculated using measurements from the flow rate sensor and from the size of the container.

9. The dialysis machine of claim 1, comprising a user interface configured to prompt a user to input a prescription comprising a prescribed flow rate and a prescribed bicarbonate.

10. The dialysis machine of claim 9, wherein the data processing apparatus is configured to determine the estimated time at which the bicarbonate will be depleted using the flow rate sensor, the size of the container, and the prescription inputted by a user.

11. The dialysis machine of claim 9, wherein the data processing apparatus is configured to notify the user via the user interface if a treatment time, determined from the prescription, is longer than the estimated time at which the bicarbonate will be depleted.

12. The dialysis machine of claim 1, wherein the flow rate sensor, the pressure sensor, and a conductivity sensor are configured to provide feedback to the data processing apparatus.

13. The dialysis machine of claim 12 wherein the visual representation of the estimated time at which the bicarbonate will be depleted is updated using the feedback of the flow rate sensor, the pressure sensor, and the conductivity sensor.

14. The dialysis machine of claim 12, wherein a leak from the container can be detected using the feedback from the flow rate sensor, the pressure sensor, and the conductivity sensor.

15. The dialysis machine of claim 14 wherein the leak is detected by the pressure sensor measuring a decrease in pressure outside a threshold.

16. The dialysis machine of claim 1, wherein the flow rate sensor comprises a volumetric pump.

17. The dialysis machine of claim 1, wherein the fluid source comprises a volumetric chamber.

* * * * *